(12) United States Patent
Yatom et al.

(10) Patent No.: US 12,707,555 B2
(45) Date of Patent: Aug. 11, 2026

(54) LOW-TEMPERATURE DIELECTRIC BARRIER DISCHARGE DEVICES

(71) Applicant: The Trustees of Princeton University, Princeton, NJ (US)

(72) Inventors: Shurik Yatom, Lawrenceville, NJ (US); Yevgeny Raitses, Princeton, NJ (US); Sophia Gershman, Scotch Plains, NJ (US); Phillip Efthimion, Bedminster, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 1019 days.

(21) Appl. No.: 17/669,622

(22) Filed: Feb. 11, 2022

(65) Prior Publication Data

US 2023/0262867 A1 Aug. 17, 2023

(51) Int. Cl.
*H05H 1/24* (2006.01)
*A61L 2/14* (2006.01)

(52) U.S. Cl.
CPC ............. *H05H 1/2406* (2013.01); *A61L 2/14* (2013.01); *A61L 2202/11* (2013.01); *H05H 2245/40* (2021.05)

(58) Field of Classification Search
CPC ................................ A61L 2/14; H05H 1/2406
See application file for complete search history.

(56) References Cited

U.S. PATENT DOCUMENTS

2015/0137677 A1* 5/2015 Sohn ........................ H01T 19/04 313/268
2020/0016286 A1* 1/2020 Clack ........................ A61L 2/14
2021/0112651 A1* 4/2021 Lee ...................... A61N 1/0428

OTHER PUBLICATIONS

Boekema et al., "A new flexible DBD device for treating infected wounds: in vitro and ex vivo evaluation and comparison with a RF argon plasma jet", J. Phys. D: Appl. Phys., vol. 49, 044001, 2016.

Xia et al., "Inactivation of Airborne Porcine Reproductive and Respiratory Syndrome Virus (PRRSv) bu a Packed Bed Dielectric Barrier Discharge Non-Thermal Plasma", J. Hazard. Mat., 393, 122266, 2020.

Aboubakr et al., "Virucidal Effect of Cold Atmospheric Gaseous Plasma on Feline Calicivirus, a Surrogate for Human Norovirus", Applied Environmental Microbiology, vol. 81, No. 11, pp. 3612-6622, 2015.

(Continued)

*Primary Examiner* — Kevin Joyner
(74) *Attorney, Agent, or Firm* — Meagher Emanuel Laks Golberg & Liao, LLP

(57) ABSTRACT

Disclosed are dielectric barrier discharge (DBD) devices and methods of use for sterilizing surfaces. The DBD devices generally include one or more first electrodes, one or more second electrodes or chemical reagent layers, and at least one dielectric layer between the one or more first electrodes and the one or more second electrodes or chemical reagent layers. In various configurations, the at least one dielectric layer is either (a) in contact with at least one of the first electrodes or (if present) at least one chemical reagent layer, or (b) is separated from the one or more first electrodes by a first gap and is also separated from the one or more second electrodes or chemical reagent layers by a second gap.

11 Claims, 10 Drawing Sheets

(56) References Cited

OTHER PUBLICATIONS

Wu et al., "MS2 Virus Inactivation by Atmospheric-Pressure Cold Plasma Using Different Gas Carriers and Power Levels", Applied Environmental Microbiology, vol. 81, No. 3, pp. 996-10021, Feb. 2015.
Pradeep et al., "Non-thermal plasmas (NTPs) for inactivation of viruses in abiotic environment", Res. J. Biotech., vol. 11, No. 6, pp. 91-96, Jun. 2016.
Shi et al., "Effect of Low-Temperature Plasma on Deactiveation of Hepatitis B Virus", IEEE Trans. Plasma Sci., vol. 40, No. 10, pp. 2711-2716, Oct. 2012.
Nayak et al., "Rapid inactivation of airborne porcine reproductive and respiratory syndrome (PRRS) virus using an atmospheric pressure air plasma", Plasma Process. Polym., 201900269, 2020.
Napp et al., "On the history of plasma treatment and comparison of microbiostatic efficacy of a historical high-frequency plasma device with two modern devices", GMS Hygiene and Infection Control, vol. 10, pp. 1-7, 2015.
Brandenburg, Corrigendum: Dielectric barrier discharges: progress on plasma sources and on the understanding of regimes and single filaments (2017 Plasma Sources Sci. Technol. 26 053001), Plasma Sources Sci. Technol. vol. 27, 2018.
Heise et al., "Sterilization of Polymer Foils with Dielectric Barrier Discharges at Atmospheric Pressure", Plasmas and Polymers, vol. 9, No. 1, pp. 23-33, 2004.
Powerlabs Website, powerlabs.org/plasmaglobes.htm#%C2%AOPRINCIPLE%20OF%20 OPERATION, Feb. 14, 2020 version accessible at web.archive.org/web/20200214090948/http://www.powerlabs.org/plasmaglobes.htm, last accessed Apr. 28, 2022.
Jung et al., "Wearable Atmospheric Pressure Plasma Fabrics Produced by Knitting Flexible Wire Electrodes for the Decontamination of Chemical Warfare Agents", Sci Rep 7:40746, pp. 1-9, 2017.
Laroussi et al., "Nonthermal Decontamination of Biological Media by Atmospheric-Pressure Plasmas: Review, Analysis, and Prospects", IEEE Trans. Plasma Sci., vol. 30, No. 4, pp. 1409-1415, Aug. 2002.
Boekema et al., "Antibacterial plasma at safe levels for skin cells", J. Phys. D: Appl. Phys., vol. 46, 422001, pp. 1-7, 2013.
Xia et al., "Inactivation of airborne viruses using a packed bed non-thermal plasma reactor", J. Phys. D: Appl. Phys., vol. 52, 255201, pp. 1-12, 2019.

* cited by examiner

LOW-TEMPERATURE DIELECTRIC BARRIER DISCHARGE DEVICES

STATEMENT REGARDING FEDERALLY SPONSORED RESEARCH OR DEVELOPMENT

This invention was made with government support under Grant No. DE-ACO2-09-CH11466 awarded by the Department of Energy. The government has certain rights in the invention.

BACKGROUND

There is an urgent need for wide use of sanitizing and disinfecting agents and techniques. Brought into focus the current COVID-19 pandemic, it is no longer limited to medical, pharmaceutical, or food industry, but rather expanded to the decontamination of commonly used surfaces such as doorknobs and devices, such as masks, cell phones, and pens. Over the last two decades, cold atmospheric pressure plasmas (CAP) have seen rapid development in the areas of bacterial and viral inactivation and surface disinfection. A recent review summarized the achievements of a broad range of CAP plasma sources, including dielectric barrier discharges (DBD), that effectively inactivate bacteria, viruses, fungi, and bacterial spores.

In spite of these achievements, the only sterilization method that involves plasma, which is currently recommended by the Centers for Disease Control and widely accepted in industry, is a rigid device based on plasma activation of hydrogen peroxide vapor, one of the most effective and clean germicidal chemicals, and one which utilizes vacuum chambers. See U.S. Pat. No. 4,952,370. Hydrogen peroxide does not leave any dangerous residue because its decomposition products are water and oxygen.

The disinfecting and even sterilization effectiveness of plasmas is due to their bioactive properties such as reactive oxygen (ROS) and nitrogen species (RNS), electrons, currents, electric and electromagnetic fields, and UV rays. The mechanisms of bacterial inactivation have been investigated by many groups but remain unclear. The chemical and electrical plasma properties may be affecting a bacterial cell in stages. The electrons and the electric field affect the cell membrane and aid in the cell penetration by the RNSs and some long-lived ROSs. ROS are involved in lipid peroxidation and other oxidative reactions damaging the cell membrane and aiding the transport of RNS/ROS into the cell.

Inside the cell the ROS/RNS damage proteins, lipids, and the DNA. The combined effect of these processes is bacterial cell inactivation. Most of the work on medical and biological applications of DBDs has been conducted on one of three configurations, a floating electrode configuration, a plasma jet (floating electrode or two electrode), and a less common surface DBD. In a floating electrode device, the high voltage electrode is encased in a dielectric material and the treated surface acts as a ground electrode; the treated surface is exposed to high electric fields and fluxes of charged particles. The most extensively studied is the plasma jet, which uses power from pulsed dc to microwave range and where plasma effluent is carried by a gas flow to the treated surface. The plasma effluent is suitable for medical applications but requires a compressed gas supply. Surface DBD has been primarily studied as an actuator for flow control in aeronautics applications and for large area surface modifications.

Atmospheric pressure plasmas have been shown to be effective for the decontamination of surfaces from bacteria and viruses, but the level and the rate of inactivation strongly depend on the biological species, experimental conditions, and the plasma source. For example, D-value (time for 1 $\log_{10}$ reduction) is 225 s for the exposure to the gases produced by one known DBD, 150 s for another known DBD, 35 s for *E. coli* exposed to an atmospheric pressure helium/air glow discharge, and 15 s for a paper DBD. The fast reduction D=15 s was achieved by a single-use flexible DBD device using a printed patterned electrode on a paper substrate and operated at 2 kHz, 3.5 kV AC, 10 W. This is a disposable device.

Another variation on plasma disinfection is the use of low-pressure plasma activated hydrogen peroxide vapor. Systems such as the low temperature sterilization systems by Sterlis Healthcare are widely accepted methods of sterilization of materials susceptible to high temperatures, humidity, and corrosion. In more recent studies, the addition of hydrogen peroxide has been explored to enhance plasma disinfection at atmospheric pressure. Addition of $H_2O_2$ droplets into a corona discharge produced 6 $\log_{10}$ reduction, and adding $H_2O_2$ vapor to the plasma effluent produced a reduction greater than 6 $\log_{10}$ in the bacterial load and a significant reduction in biofilm and spores. The dominant mechanisms responsible for the enhancement depend on the type of plasma, the state of $H_2O_2$. $H_2O_2$ vapor is ionized in a plasma to form $H_2O_2^-$, while droplets may be negatively charged, a water solution of $H_2O_2$ is subject to the active species introduced by plasma into the solution akin to plasma activated water. Pure water is acidified by plasma enhancing the bactericidal effects, while buffered solutions such as phosphate buffer saline (PBS) maintain the pH level but are affected by the dissolved ozone, nitrates, and hydrogen peroxide radicals.

This diversity of results and conditions indicate a dielectric barrier discharge that is safe to touch, has long-term operational stability, and does not require external gas supplies or sophisticated power sources is both useful and desirable.

BRIEF SUMMARY

Disclosed are dielectric barrier discharge (DBD) devices that operate at safe temperatures, have long-term operational stability, and do not require external gas supplies or sophisticated power sources. The DBD devices generally comprise one or more first electrodes, one or more second electrodes or chemical reagent layers, and at least one dielectric layer between the one or more first electrodes and the one or more second electrodes or chemical reagent layers. The at least one dielectric layer will either (a) be in contact with at least one first electrode or (if present) at least one chemical reagent layer, or (b) be separated from the one or more first electrodes by a first gap and separated from the one or more second electrodes or chemical reagent layers by a second gap.

Optionally, the DBD device uses one or more second electrodes, which are each configured as a wire or a patterned metal layer.

Optionally, the DBD device includes a first semipermeable layer in contact with an outward-facing surface of the first electrode, a second semipermeable layer in contact with the outward-facing surface of the one or more second electrodes, or both, either of which may optionally be, e.g., a dielectric fabric or mesh.

Optionally, the DBD device is powered by a portable power supply, and/or may be configured to operate continuously at a current less than or equal to 2 mA.

Optionally, the temperature of the DBD device during operation is between about 22° C. and about 40° C.

Optionally, the DBD device comprises one or more first electrodes, one or more dielectric layers, and one or more chemical reagent layers. In some of those embodiments, the device further comprises an additional electrode separated from the chemical reagent layer by a fixed gap, and/or a screen between the first electrode and the chemical reagent layer, the screen being separated from the first electrode by a first gap, and wherein the chemical reagent layer is in contact with the screen.

Optionally, the DBD device has an internal volume defined by the dielectric layer (e.g., when the dielectric layer is shaped as a jar or container wall), where the internal volume is filled with a gas or gas mixture capable of generating excimer molecules and UV-C during a discharge by the device.

Also disclosed is a method for sterilizing surfaces, the method first involving providing a disclosed DBD device. The DBD device is used to generating a cold homogenous plasma by forming a discharge path from the one or more first electrodes, to the at least one dielectric layer, and from the at least one dielectric layer to the one or more second electrodes or chemical reagent layers, to ground. The cold plasma induces reactive species to form on a contaminated surface by contacting the contaminated surface with cold homogenous plasma, the contaminated surface containing biological contaminants, such as bacteria, viruses, or a combination thereof. The reactive species are allowed to kill the biological contaminants. This may involve applying the plasma to the contaminated surface from a distance of, e.g., ≤1 cm, for a time period≤5 min, ≤4 min, ≤3 min, ≤2 min, ≤90 seconds, or ≤1 min.

Optionally, the method may also involve introducing a layer of liquid (e.g., comprising water, $H_2O_2$, etc. that can form ROS or RNS species) between the dielectric barrier discharge (DBD) device and the surface, the liquid configured to amplify the plasma-induced chemistry. In some cases, the DBD device is applied at a distance from the liquid, while in others, the DBD device is applied directly to the liquid.

DETAILED DESCRIPTION

The disclosed dielectric barrier device can generally be considered as requiring three basic components. There is one or more first electrodes (which may be in a variety of forms, including wires, plates, patterned metal layers, etc.), which are separated from one or more second electrodes (which may also be in a variety of forms, including wires, patterned metal layers, etc.) or chemical reagent layers. The dielectric layer(s) are between the first electrode(s) and the second electrode(s) or chemical reagent layer(s). In some embodiments, the dielectric layer(s) are in contact with the first and/or second electrodes or chemical reagent layers, while in others, the dielectric is separated by from each of the first electrode(s) and the second electrode(s) or chemical reagent layer(s) by defined gaps. Plasma will be generated that is capacitively coupled with displacement current between, e.g., the first electrodes and a ground through the dielectric layer and the second electrodes or chemical reagent layer.

Figure 1:
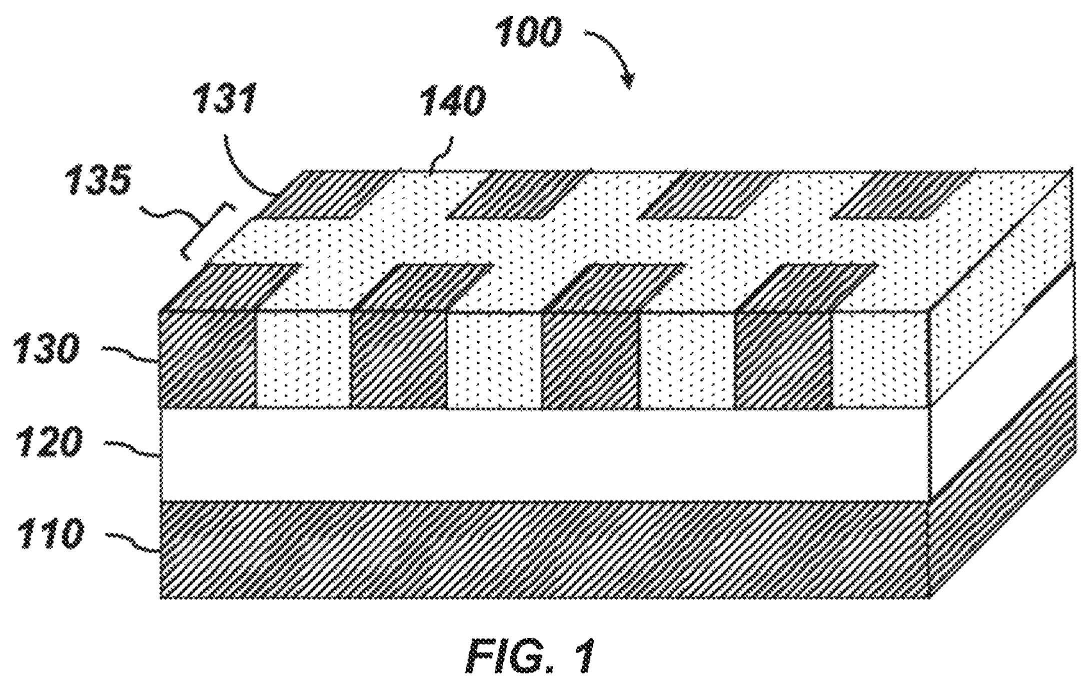
FIG. 1 is a depiction of a discharge cell for a dielectric barrier discharge device.

One example of this can be seen with reference to FIG. 1, where a cross-sectional view of a portion of an example discharge cell (100) of a DBD device can be seen. When not in operation, the discharge cell (100) comprises, consists essentially of, or consists of three basic components: a first electrode (110), where the top surface of the electrode is in contact with one or more dielectric layers (120). A power supply (not shown) may also optionally be incorporated into the device. A top surface of the dielectric layers is in contact with a patterned second electrode (130, 131). The first electrode will preferably be connected to a high voltage source (not shown) and the second electrode will preferably be grounded (not shown).

The first and second electrodes may be independently comprised of any appropriate conductive material, including a metal, an alloy, an electric conductive compound, or a combination thereof. The first electrode may be a single layer of a conductive material. Specific examples of such electrode materials include copper, sodium, sodium-potassium alloy, magnesium, lithium, magnesium/copper mixtures, magnesium/silver mixtures, magnesium/aluminum mixtures, magnesium/indium mixtures, aluminum/aluminum oxide ($Al_2O_3$) mixtures, indium, lithium/aluminum mixtures, rare earth metals, and the like. Preferably, the first and second electrodes are configured to have some degree of flexibility/non-rigidness.

The one or more dielectric layers may be comprised of any appropriate dielectric material, although preferably the layers are comprised of a flexible/non-rigid material. For example, the dielectric layers may be comprised of, e.g., a polyimide, a polyamide, polytetrafluoroethylene (PTFE), polyethylene (PE), polypropylene (PP), a silicon-based material, quartz, glass, or other dielectric materials known to one skilled in the art, although quartz and glass are not preferred.

The disclosed discharge cells are generally thin, such as ≤5 cm thick, ≤3 cm thick, ≤1 cm thick, or ≤5 mm thick.

Referring back to FIG. 1, when current passes from the first electrode, through the dielectric layer, and through the patterned second electrode, plasma (140) that is capacitively coupled with the displacement current, generally forming in and around the patterned electrodes (130, 131), such as in the gaps (135) between the electrodes.

The discharge cell is powered by a power supply, which may optionally be a portable power supply. Any appropriate power supply is envisioned. In some embodiments, the power supply is configured to provide a current that is less than or equal to 2 mA. The power supply is connected to the electrodes using any appropriate means, including via, e.g., wire, conducting thread, or conducting tape. The opposite electrodes are connected to group via any appropriate means, including via, e.g., The power supply is connected to the electrodes using any appropriate means, including via, e.g., wire, conducting thread, conducting tape, or fabric strips at the ends of the fibers.

In some embodiments, the power supply is controlled or configured to provide current such that the temperature of the device is maintained at less than 50° C., or less than 40° C. In some embodiments, the power supply is controlled or configured to provide current such that the temperature of the device is maintained at between about 15° C. and about 50° C., and more preferably between about 22° C. and about 40° C.

Example 1

One example of a flexible DBD (flex-DBD) was based on a printed circuit design, and consisted of a layer of copper tape (0.127 mm thick, 16 mm×26 mm) serving as a high voltage electrode (e.g., a first electrode). That copper tape was covered by a layer of Kapton® polyimide tape (DuPont) (100 μm thick, $\epsilon_{rel}\approx 3.5$) that contains an adhesive (e.g., the dielectric layer, connected/attached to the first electrode via an adhesive layer). A patterned ground electrode (30 μm thick) was electroless nickel immersion gold (ENIG) coated onto the polyimide tape. The pattern on the ground electrode consisted of 200 (10×20) square cavities, each 0.75 mm×0.75 mm in size.

A regulated, 500 V-10 kV, 25-60 kHz, pulsed AC power source (PVM 500 AC, Information Unlimited) was used to generate the discharge. The patterned electrode of the flex-DBD was connected to the power-supply ground, and the copper foil electrode to the power-supply high voltage output transformer. A Tektronix D (2 GS/s, 250 MHz) oscilloscope was used to monitor the current, voltage, and charge transfer in the circuit during experiments: current to ground (Pearson Model 2877 Current Monitor, 1 V/A, 2 ns rise time); voltage at the high voltage (copper tape) electrode (Tektronix P6015 HV probe); and charge transferred was determined by measuring the voltage across a 10 nF capacitor ($C_M$) connected in series on the ground side of the flex-DBD.

The flex-DBD was operated in resonance mode. The parallel connection between the DBD and the secondary coil on the high voltage output transformer has a resonance frequency, $$\approx \frac{1}{2\pi\sqrt{LC}},$$

where L is the inductance of the secondary and C is the capacitance of the flex-DBD.

Figure 2:
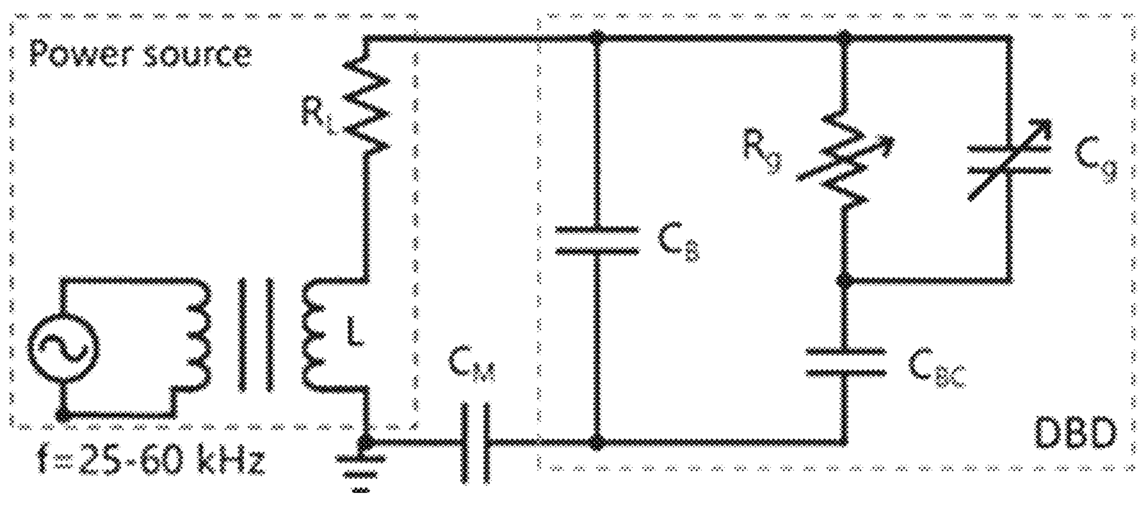
FIG. 2 is a diagram of an equivalent circuit used in an experiment with an embodiment of a dielectric barrier discharge device.

FIG. 2 is a diagram of the equivalent circuit to that used in this example, where $C_B$ is the capacitance of the flex-DBD device excluding the rectangular cavities, $C_{BC}$ is the capacitance of the solid portion and $C_g$ and $R_g$ are the capacitance and resistance of the open air portion of the cavities, $C_M$ is the measurement capacitor, and L and $R_L$ are the inductance and the resistance of the secondary coil of the high voltage transformer of the high frequency power source.

During operation the capacitance of the flex-DBD is approximately, $C\approx C_B+C_{BC}$. At the resonance frequency, the overall impedance of the L-C circuit as seen by the power source is at a maximum, therefore minimizing the current drawn and hence the power used by the device, and maximizing the voltage applied to the DBD, facilitating a discharge at lower power used by the power source.

To start the device, the frequency was adjusted to a resonance value at a voltage amplitude below the starting voltage, then increased the applied voltage to the start the discharge (here, $V_{start}$=1.9 kV amplitude), and readjusted the frequency to a new resonance value for the flex-DBD with the plasma on. The voltage was then increased until the entire surface of the flex-DBD appeared to glow to the naked eye (2.8 kV). The resonance operating frequency was 42±2 kHz. The variation in the resonance frequency is likely due to the slight differences in the hand-made devices and the operating conditions. The temperature of the grounded glowing face of the flex-DBD was monitored for several minutes prior to starting experiments to ensure that a steady-state condition was reached, and continued to monitor the temperature during experiments. Voltage amplitude and duty cycle were adjusted to maintain the temperature below 50° C. in steady-state operation. Except for the low power trial at 2 kV, further disinfection experiments were conducted with a voltage amplitude of 3 kV, a displacement current amplitude of 50 mA, a duty cycle of ~20%, and pulse repetition rate of 1 kHz. The voltage, current, and charge measurements were conducted during the sterilization experiments.

In one experiment, a 40 kHz sinusoidal voltage, amplitude of 1.9-3 kV, was applied to the high voltage electrode for ~200 μs (20% duty cycle at 1 kHz repetition rate). A surface dielectric barrier discharge ignited inside the cavities and around the perimeter of the flex-DBD. The discharge propagated along the surface of the dielectric and eventually eroded the substrate of the ground electrode. The erosion pattern observed on post-run devices indicated that the discharge occurs in the center portion of each cavity leaving the angles intact. This is due to the electric field topology in the cavity with the maximum electric field E=V/r~80 kV/cm, at the center of the circular cavity with a given radius (r). The erosion of the substrate of the patterned electrode happened over months of operation, possibly because only a few cells are lit at any time. During the discharge, the maximum current can be up to 100 mA for several tens of ns.

Water can form a conductive film that prevents charge accumulation on the electrode, preventing breakdown conditions. This effect depends on the voltage rise time and breakdown voltage may be reached at sub-nanosecond rise times. However, in the flex-DBD, the voltage rise time is ~7

μs, too slow to prevent the charge leakage from the conductors. The parts of the device that become moist will not light until dry. If that occurs when the power is on, heating due to the resistive and dielectric losses will self-dry the device and it will restart once the moisture evaporates. A water resistant material was used in experiments with $H_2O_2$ solutions, to prevent the flex-DBD becoming wet while allowing active species from the plasma to reach the treated surface. This sensitivity to water is important for bio-related applications.

Figure 3:
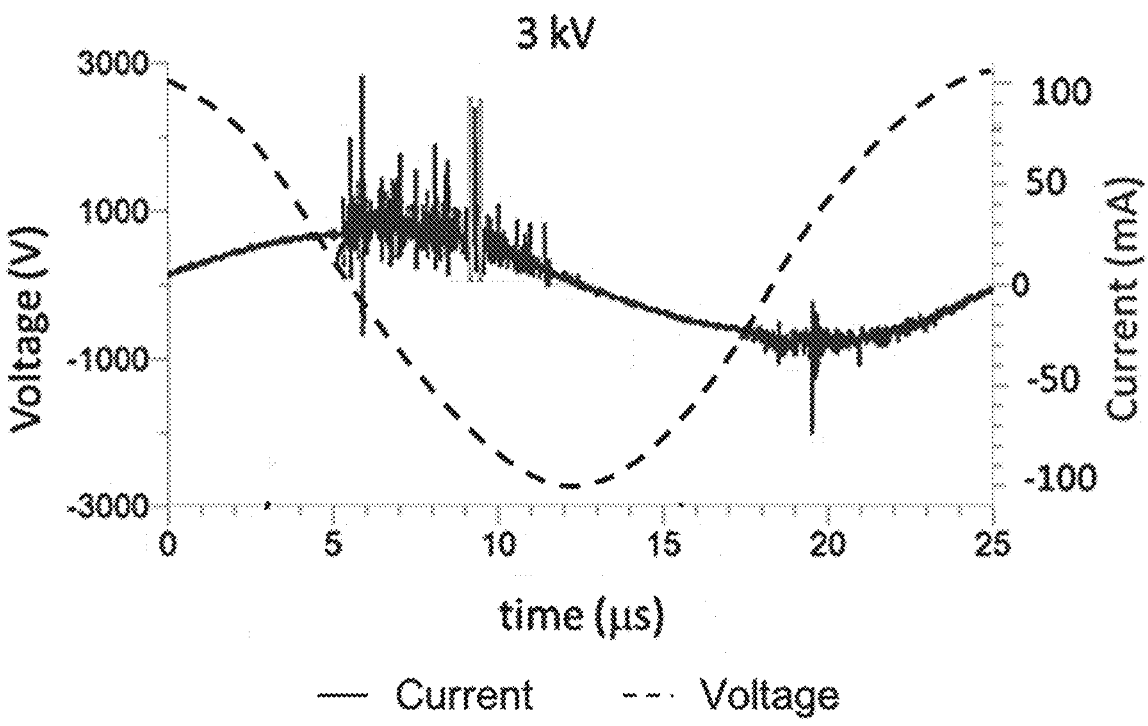
FIG. 3 is a graph showing example current and voltage traces for one AC cycle.
Figure 4:
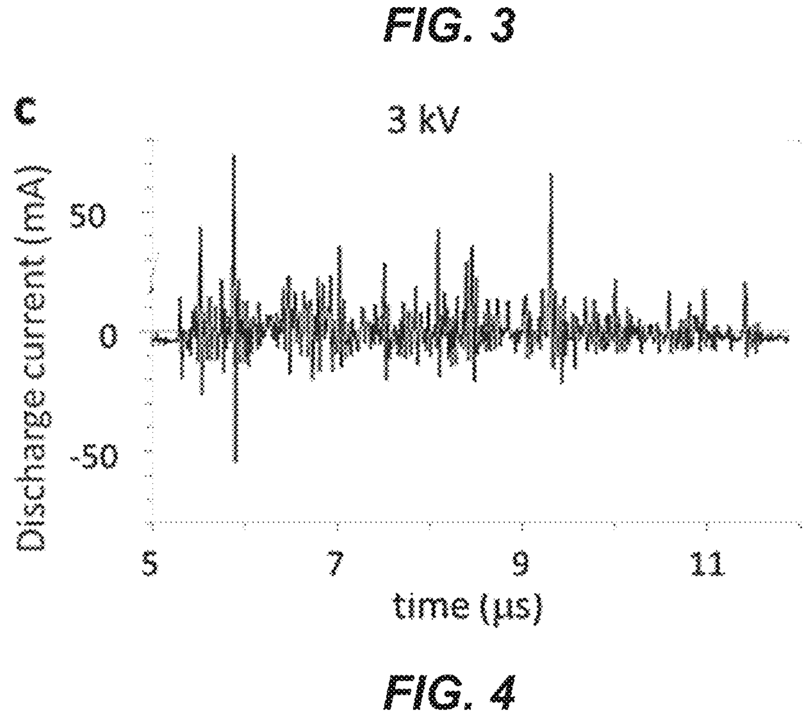
FIG. 4 is a graph showing an example discharge current for one quarter of the cycle for applied voltage amplitudes of 3 kV.

Referring briefly to FIGS. 3 and 4, a typical current trace is comprised of a displacement current sinusoidal component of (42±2) kHz and the superimposed sharp spikes 10-50 ns in duration corresponding to the discharges (FIG. 3). The displacement current was subtracted from the total measured current to obtain the discharge current (FIG. 4). The number of discharges, their overall duration, and their amplitude increase with increasing voltage. Although at 3 kV, the flex-DBD appeared completely lit, fast imaging triggered on a current spike demonstrates that during each current spike only a few bright regions are observed. Individual current spikes appear to correspond to isolated discharge events that appear randomly on the surface of the DBD. The number and the amplitude of the current spikes is not symmetrical in each half cycle of the AC current/voltage with a greater number of spikes occurring during the time when the mesh electrode acts as the anode, the voltage applied to the copper tape electrode is negative.

In case of a positive mesh electrode, the electrons are able to flow into the anode and the current grows, but if the mesh electrode is negative, the electrons accumulate on the dielectric and the current stops resulting in lower current spikes. This asymmetry has been observed in plasma actuators that are a single edge surface DBD similar to the example flex-DBD.

The number of individual discharges or current peaks varies depending on the maximum applied voltage (overvoltage). For example, the number of current peaks (over 10 mA) is 15±8 at 2 kV and increases to 45±8 for 3 kV.

The greater number of current spikes results in a greater amount of charge transferred in the circuit as evident from a Lissajous plot. The Lissajous plot has a two-slope shape with a slight asymmetry due to a greater number of more intense discharges for the negative voltage (positive patterned electrode). The energy dissipated in the circuit per one cycle can be calculated as the area of the Lissajous plot, and the power, P, is then determined using the frequency, f, the duty cycle, v: $P=f\nu\int QdV$, where Q is the charge measured by the capacitor probe and dV is the voltage obtained by the high voltage probe.

Figure 5:
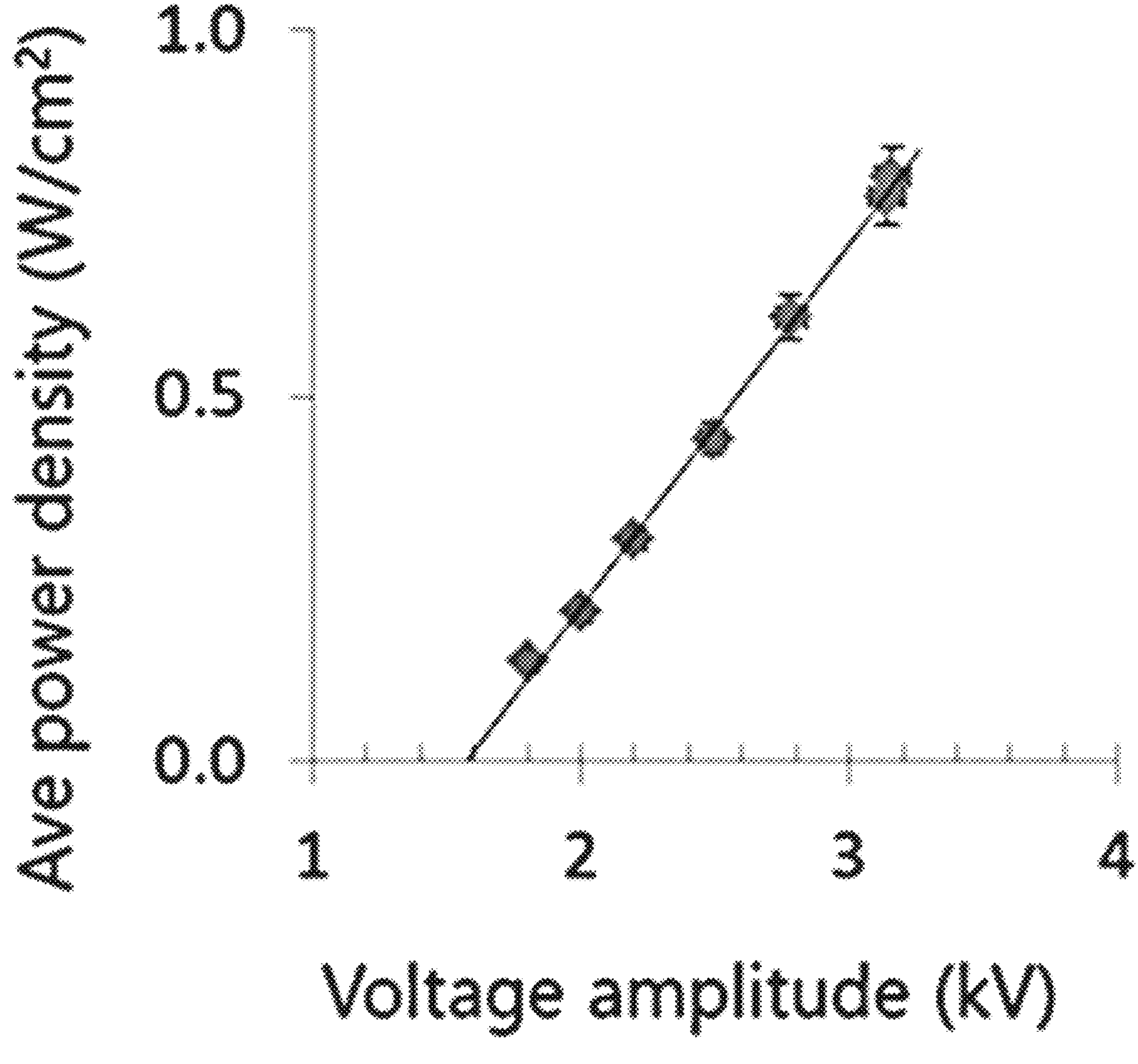
FIG. 5 is a graph showing that the average power increases linearly as a function of the applied voltage amplitude when the duty cycle and the frequency were kept constant at 20% and 40 kHz respectively.

For example, for the peak voltage of 1.9 kV the energy per cycle was 0.04 mJ/cycle. For the frequency of 41 kHz and a 20% duty cycle this gives the power of 0.3 W. For the max voltage of 2.9 kV the energy per cycle was 0.14 mJ/cycle, and the power, 1.1 W. The corresponding power density for the ~2 $cm^2$ device is 0.15-0.5 $W/cm^2$. The applied max AC voltage was varied from 1.6 kV to about 3 kV while keeping the frequency and the duty cycle constant. The resulting power varied linearly (see FIG. 5) with the applied voltage, which can be used as a calibration curve to set the desired power for a given device. Increasing the operating voltage increases the discharge power and corresponds to an increase in the number of individual discharges and the production of plasma. Increasing the duty cycle increases the overall power consumption by the device, but does not change the number of individual discharges per cycle.

Figure 6:
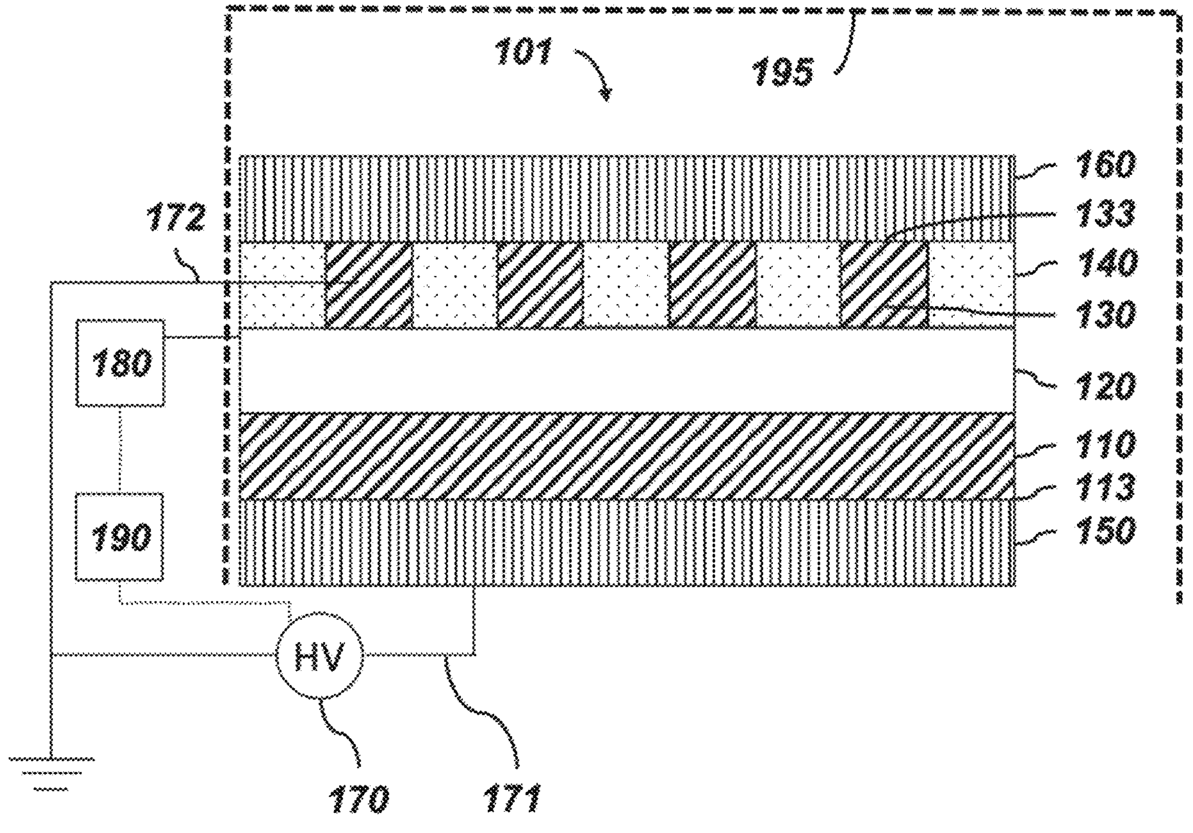
FIG. 6 is a cross-sectional view of a dielectric barrier discharge device with optional semipermeable membranes.

Referring to FIG. 6, an alternate discharge cell for a dielectric barrier discharge (DBD) device can be seen, where the discharge cell (101) comprises, consists essentially of, or consists of not only the first electrode (110), dielectric layer(s) (120) and second electrodes (130) as described previously, but also one or more additional layers. In particular, the device (101) may optionally contain a first semipermeable layer (150) in contact with an outward-facing surface (113) of the first electrode (110). The device (101) may optionally contain a second semipermeable layer (160) in contact with an outward-facing surface (133) of the one or more second electrodes (130). The device (101) may contain both a first and second semipermeable layer, just a first semipermeable layer, or just a second semipermeable layer, as appropriate. The first and second semipermeable layers may take any appropriate form, including, e.g., a dielectric fabric or mesh.

As seen in FIG. 6, the first electrode is electrically connected (171) to the high voltage source (170), while the second electrodes are grounded (172).

In addition, one or more surfaces or portions of the device (101) may also have their temperature or other parameter measured or monitored, periodically or continuously, by a temperature sensor (180). Here, a surface of the dielectric layer is shown as being monitored by the sensor. Any appropriate sensor, such as a thermocouple, may be utilized.

One or more processors or control circuitry (190) may be present for controlling the discharge cell and/or the entire device. The processors or control circuitry may be operably connected to the temperature sensor (180) and the power supply (170). The processors or control circuitry may be configured to maintain an appropriate operating temperature, as discussed previously. The processors or control circuitry may be configured to have an automatic safety shut-off, if the temperature is detected as being outside a target range, or exceeding a threshold. The safety shut-off may also be configured to occur if the voltage or current exceeds certain thresholds.

An enclosure, such as a partial enclosure (195) can be provided around at least a portion of the discharge cell and a target surface to be disinfected. Doing so allows plasma products, such as ozone, nitric or nitrous oxides of all kinds, to accumulate in the contained volume.

Generally, gaps between the electrodes and a target surface to be disinfected should be ≤2 mm, such as between 1 μm and 2 mm, although larger gaps may be possible (≤2 cm, ≤1 cm, ≤5 mm, etc.) if an enclosure partially surrounding the discharge cell and the target surface is utilized.

Figure 7:
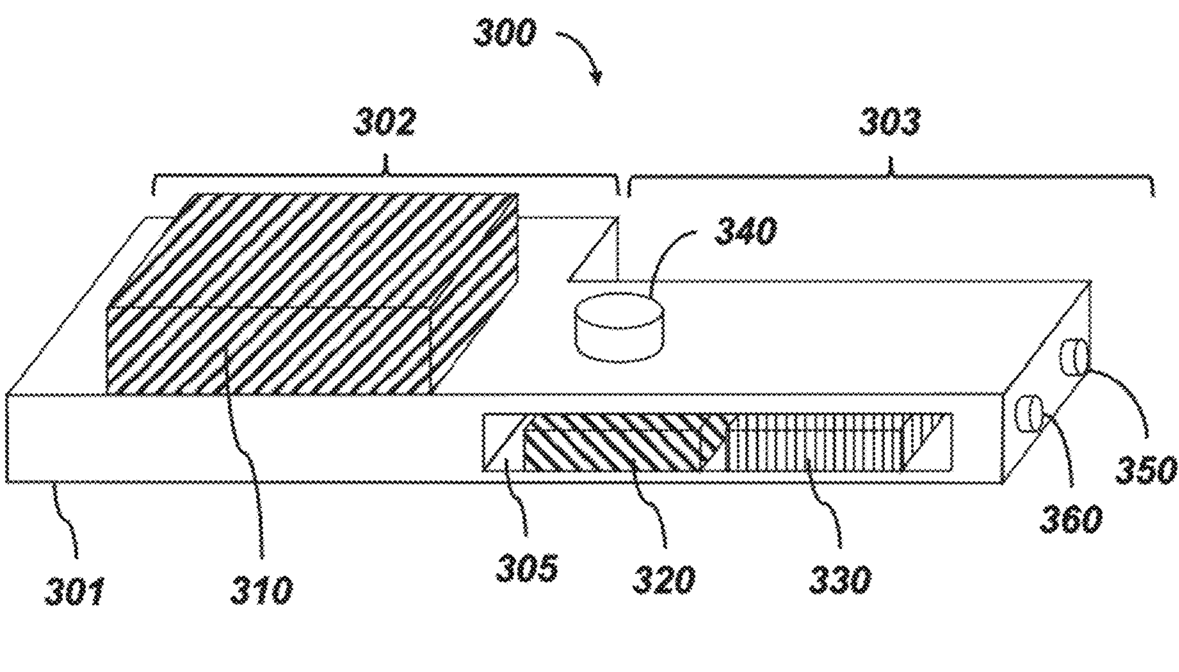
FIG. 7 is a depiction of a hand-held dielectric barrier discharge device.

Referring briefly to FIG. 7, it is understood that it may be useful in some cases to provide a housing for parts of the device. FIG. 7 shows a cross-sectional view of a DBD device (300), where the device comprises a housing (301) to which the discharge cell (310) may be attached, embedded, or otherwise operably connected. The housing (301) which may optionally have a first portion (302) and a handle portion (303).

The first portion (302) may be the part of the housing that connects or attaches to the discharge cell (310). For example, the device may be welded, bonded, adhered, or bolted to an outer surface of the housing (301).

The handle portion may define an internal cavity (305), where electronics or other sensitive components may be contained. For example, the internal cavity may contain a power supply (320), such as batteries and the necessary power supply circuitry, and a processor and/or control circuitry (330) for controlling the discharge cell (310). Optionally, the processor and/or control circuitry comprises a wired and/or wireless communication interface, and the processor/control circuitry can be used to control wired or wireless communication with, e.g., remote data store or a remote processor (not shown). In some cases, the remote processor may be a mobile device, a server, a laptop, or a desktop computer.

The housing may also include openings to allow one or more switches or controls (340) to be utilized as part of the tool, e.g., for allowing a user to activate or deactivate the DBD device (310) with a switch. The housing may also include openings to allow for one or more lights, displays, or indicators (350). For example, an LED could activate when the device is powered on, another LED could activate when the device is at stable operating conditions, etc.

The housing may also include one or more ports (360) that allow for, e.g., a data connection, a power connection, etc.

These devices are preferably free of any additional gas supply or sophisticated power sources.

These devices are capable of long-term stable operation (i.e., at least a month, preferably at least 2 months, and more preferably at least 3 months).

Other variations of the disclosed device comprise a first electrode, a chemical reagent layer, and optionally an additional electrode. A Chemistry Enhanced Plasma Sterilizer (CEPS) disclosed herein in a preferred embodiment provides sterilization and disinfection of bio-contaminated surfaces.

A CEPS allows for 1) a combination and synergy of bioactive plasma properties (chemically active radicals, UV, electric field at the plasma-surface interface, surface charging, current) with a large area of the surface treatment, and 2) the presence of a layer of wet (liquid or gel or sprayed droplets) chemical reagent (e.g., water or $H_2O_2$ or their solution) between the electrode and the treated surface to enhance the generation of chemical radicals (e.g., O, OH). Further, a CEPS does not require a gas flow.

A CEPS uses a wet layer of chemical reagent/s (e.g., water, $H_2O_2$) to enhance generation of chemically active radicals important for sterilization. In addition, a CEPS can be, for example, spherical and treat a larger surface area. The large area of treatment by the CEPS can be facilitated through the optimization of the frequency and voltage of the discharge and the electrode configuration. Moreover, unlike conventional devices which have a return current path through a human body, in some embodiments, the CEPS can have two electrodes with one of these electrodes grounded.

Figure 8A:
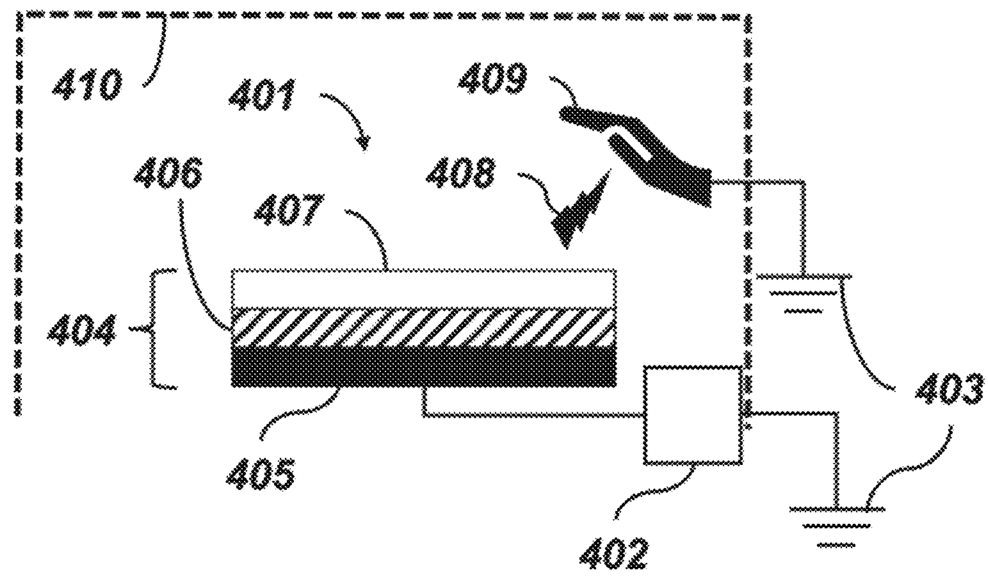
FIG. 8A is a depiction of an alternate planar dielectric barrier discharge device.

The most basic CEPS configurations are shown in FIG. 8A. The planar DBD-type CEPS (401) shown in FIG. 8A comprises, consists essentially of, or consists of a high frequency power supply (402) and a discharge cell (404). The high voltage output of the power supply (402) is applied to an electrode (405) of the discharge cell (404), with respect to ground (403). The electrode (405) is covered with dielectric layer (406) to prevent the arcing and limit the discharge current between this electrode and the ground (403) when the high voltage is applied. The electrodes and dielectric layers are as described previously.

The dielectric layer is covered with a wet (liquid) chemical reagent layer (407) such as water, $H_2O_2$, or a combination thereof. This is to enhance the generation radicals when this layer is contact with the plasma discharge (408). This plasma is capacitively coupled with the displacement current flown between the high voltage electrode (402) and the ground (403) through the dielectric layer (406), wet layer (407), plasma (408) in the air gap, and grounded target (409) (here, a human hand).

The gap between the dielectric layer and the target surface must be large enough not to get the surface wet from whatever is being treated, but close enough to allow the target surface to interact with generated plasma products. Thus, the gap will often depend on the amount of air flow or free circulation around the plasma being generated. In cases where there is relatively large air flow or free circulation, the gap will be small. Typically, this gap will be no more than a few millimeters, such as ≤3 mm, between 1 μm and 2 mm, between 1 mm and 2 mm, etc.

When there is relatively little air flow or free circulation, the gap can be larger. For example, a greater gap is possible if the device and the target surface are partially enclosed (e.g., in optional enclosure (410) which is only open on the bottom) in a contained volume (e.g., the volume defined by optional enclosure (410)), to allow plasma products, such as ozone, nitric or nitrous oxides of all kinds, to accumulate in the contained volume. In such cases, larger gaps, including gaps ≤2 cm, and preferably ≤1 cm, and more preferably ≤5 mm, are possible.

The enhanced formation of radicals due to the chemical reagent layer (407), displacement current and the charging of the interface between the plasma (408) and human skin (409) contribute to sterilization of human skin in contact with the plasma.

Figure 8B:
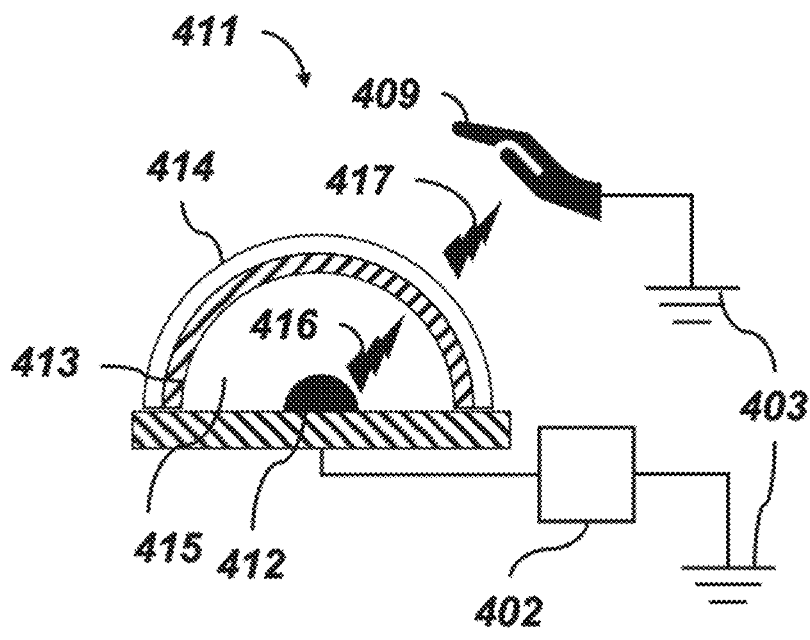
FIG. 8B is a depiction of an alternate hemispherical dielectric barrier discharge device.
Figure 8C:
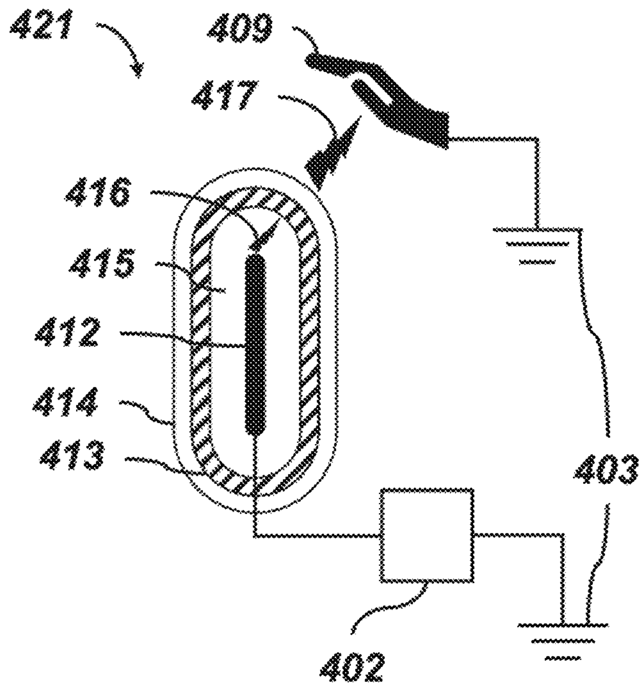
FIG. 8C is a depiction of an alternate dielectric barrier discharge wand device.

FIGS. 8B and 8C show a two-stage configuration of the disclosed CEPS of spherical and wand configurations, respectively. In these configurations, CEPS utilizes two discharges in series (two-stage discharge) to increase the treated area and/or to enhance the safe operation by limiting the maximum current in the discharge, or to assist the chemically enhanced plasma sterilization with UV generation (e.g., UV-C).

The two-stage CEPS includes two capacitively coupled discharges in series. In these figures, the first stage discharge is organized in, e.g., an internal volume (415) is formed via, e.g., a container or jar (413), where the internal volume (415) is filled with near atmospheric pressure gas or gas mixture (e.g., Argon, Neon, a mixture of gasses, etc.). The container or jar (413) is preferably made from a non-porous, rigid dielectric material (such as glass or quartz). In operation, the first discharge (416) is organized between the high voltage electrode (412) and the jar (413). This discharge and dielectric limit the current between the high voltage electrode and the ground (403). To have a large surface area of the treatment, the wall or walls that form the jar (413) are equally spaced from the high voltage electrode (412). In the spherical configuration (FIG. 8B), this can be accomplished with a hemispherical shaped jar. In this configuration, the electrode is at the center of the jar, equidistant from the jar walls. In the wand configuration (FIG. 8C), the electrode can be elongated so there is an equal distance between the outer surface of the electrode (412) and the inner surface of the wall of the jar (413) for the entire electrode.

The outer surface of the wall is coated with a thin layer of liquid chemical reagent (414). For example, water, a gel, or sprayed droplets, to enhance the generation of radicals (e.g., O, OH).

The second stage capacitively-coupled discharge (417) is organized between the jar wall (413) and the ground (403). The displacement current flows from the jar wall (413) through the chemical reagent layer (414), plasma in the air gap (417), a body (409) (e.g., a human hand) to ground (403). The enhanced formation of radicals due to the chemical reagent layer (414), displacement current and the charging of the interface between the plasma (417) and hands (or other parts of a body) (409) contribute to sterilization and disinfection of skin in contact with the plasma.

Figure 9:
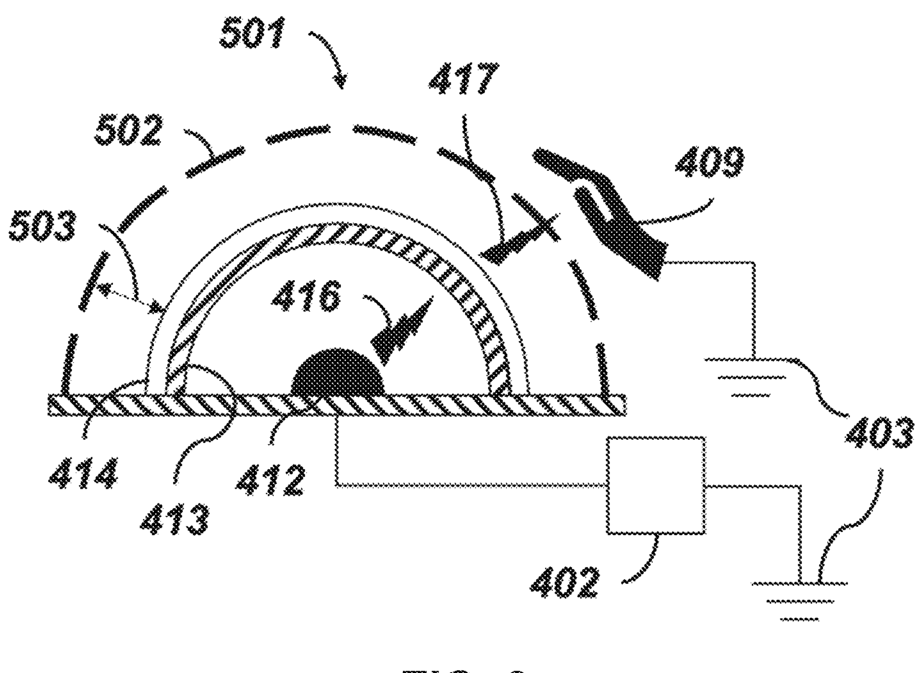
FIG. 9 is a depiction of an alternate dielectric barrier discharge device with a hand shield.

Other examples of the CEPS configurations are shown in FIG. 9. In FIG. 9, the device (501) comprises a shield layer (502) (e.g., a "hand shield") to indicate or provide a fixed gap $h_1$ (503) between the chemical reagent layer (414) and a target or subject for sterilization (409) (e.g., hands) for, e.g., optimal plasma sterilization. Such a shield could also be utilized with respect to the embodiments illustrated in FIG. 8A (where the shield would be configured as substantially parallel to dielectric layer (406), with a fixed gap) or the wand configuration of FIG. 8C.

The shield layer (502) can be fixed in place by any appropriate means. For example, the shield can be mounted to an insulating base layer, or held in place from the jar/container wall using insulating spacers.

The shield layer may be comprised of any appropriate material that still allows the generated plasma to reach the target or subject (409). The materials include, but are not limited to rigid or semi-rigid dielectric materials such as polytetrafluoriethylene (PTFE), expanded PTFE (ePTFE), polypropylene polyethylene. Preferably, the shield layer is a porous polymeric material. The shields are preferably configured as a semi-permeable fabric or gauze.

This shield is a convenient way for sterilization of human hands, as it allows to keep the discharge (417) in the air gap between the exterior side of dielectric layer (406) or container/jar wall (413) and hands.

Figure 10:
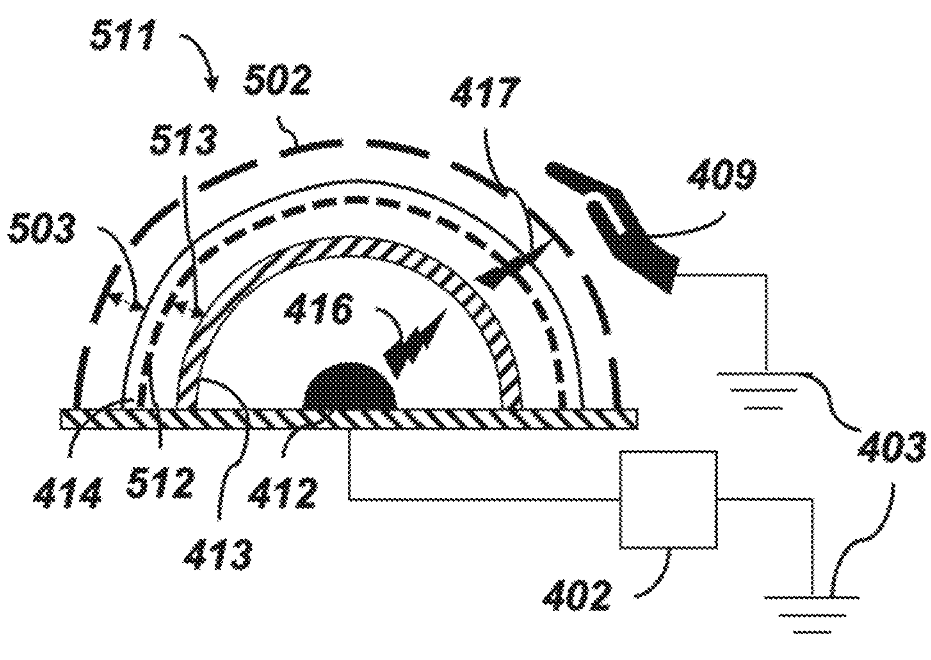
FIG. 10 is a depiction of an alternate dielectric barrier discharge device with a separate screen on which the chemical reagent layer is provided.

Alternatively, a screen is provided between the first electrode and the chemical reagent layer, the screen being separated from the first electrode by a first gap, and wherein the chemical reagent layer is in contact with the screen. As seen in FIG. 10, in some devices (511) the chemical reagent layer (414) may optionally be provided on an additional electrically floating dielectric screen (512) rather than on a dielectric coated electrode (see, e.g., FIG. 9). Such screens are dielectric screens not connected to a ground or power source (i.e., “floating”). They may be charged by plasma, and remain charged since the charge cannot leave. The screen (512) can still be capacitively-coupled to the plasma from both sides. This allows the flexibility in the use of materials for the jar and the layer holding the wet reagent. For example, the jar wall (413) has to be made from a dielectric material for capacitively coupled discharge, while the screen could be made from a conductive material.

Also, in these configurations, it is desirable that the screen (512) is made from material that has good wetting property suitable for the reagent (or is configured to have a surface with that property, e.g., via various surface treatments as appropriate). In these configurations, the requirement does not have to be applied for the jar wall (413). This approach can be used with any of the other CEPS configurations previously discussed, such as the planar or wands CEPS configurations (see FIGS. 8A, 8C).

Figure 11:
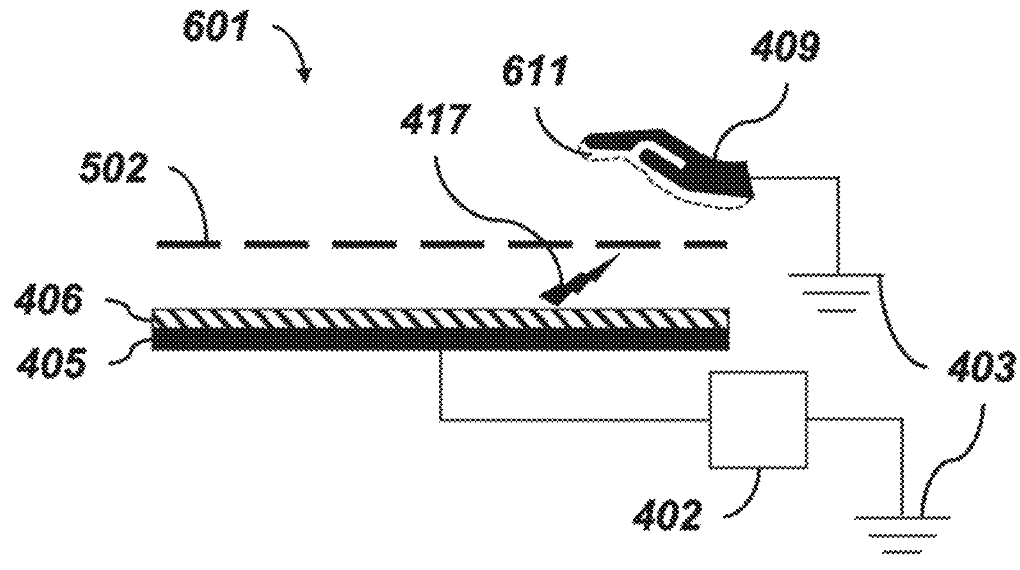
FIG. 11 is a depiction of an alternate dielectric barrier discharge device where the chemical reagent layer is applied to a target surface.

Alternatively, as shown in FIG. 11, the chemical reagent layer (611) may be applied and/or provided on the target or subject (409) (e.g., hands, treated surface, etc.) rather than on the screen (502) or on the dielectric layer (406). This approach—applying a chemical reagent layer to, e.g., hands, rather than to a screen or the dielectric layer, can be readily utilized with any of the other CEPS configurations previously discussed. In this configuration, the hands or other the surfaces may be wetted with a liquid reagent (e.g., water, $H_2O_2$, solution etc.), placed in contact with the screen, which provides the necessary gap between the hands/surface and the dielectric wall. This is important for sustaining the discharge in the air gap and for safe operation. In such configurations, the screen must provide air flow and keep the device dry. The gap is preferably between 1 μm and 2 or 3 mm.

Figure 12A:
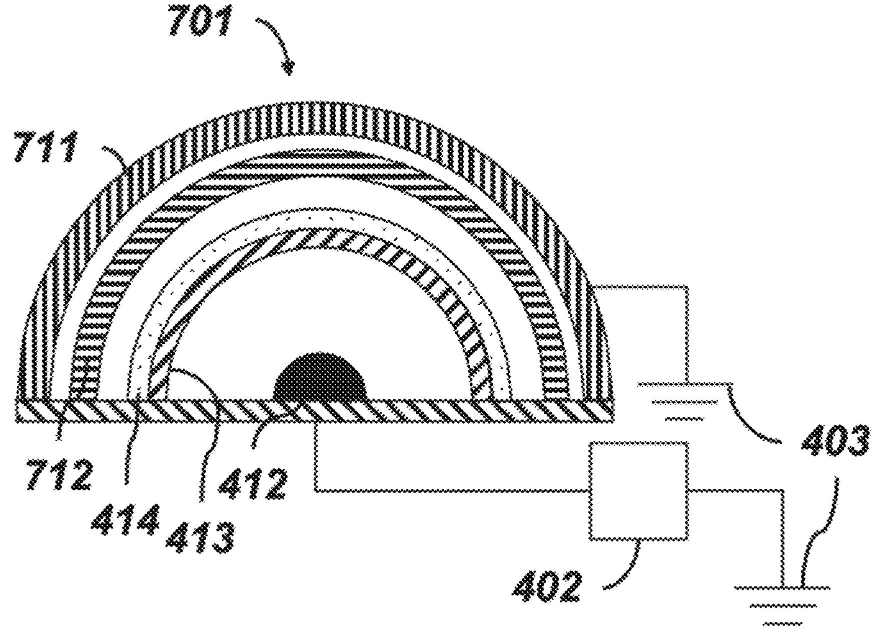
FIGS. 12A and 12B are depictions of alternate dielectric barrier discharge devices with chemical reagent layers and an additional electrode.

When dry surface sterilization of substrates is required, especially without a human being involved in the sterilization procedure, the CEPS configurations can be further modified. In particular, FIG. 12A shows one example, using an additional electrode. In the device (701) shown in FIG. 12A, the additional electrode (712) is connected to ground (403). The electrode is configured to be a fixed distance from the chemical reagent layer (414) and the dielectric layer or container/jar wall (413). One or more articles or substrates (714) (e.g., fabrics, face masks, cloth, medical bandages, gloves, etc.) can be placed between the additional electrode (711) and the chemical reagent layer (414). The current path of the discharge is between high voltage electrode (412), through the container/jar (413) (or through a dielectric layer for the planar discharge such as that in FIG. 8A or 11), then through the chemical reagent layer (414), the plasma in the air gap, through the substrate (712) to the ground electrode (711).

Figure 12B:
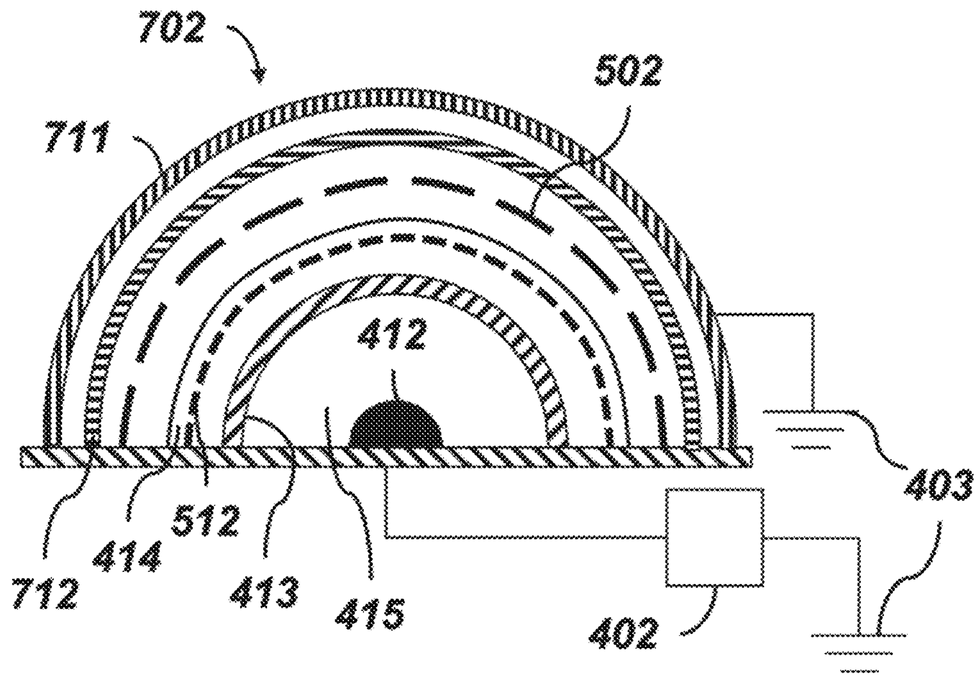

The above variations can be combined in various manners. For example, as seen in FIG. 12B, in some embodiments, a shield (502) can be used to prevent the substrate (712) touching the wet layer of chemical reagent (414). This can also be applied to the planar or wand configurations. Moreover, screen (512) can be used to keep the chemical reagent layer (414) at the distance from the dielectric wall (413). This can also be applied to the planar or wand configurations.

For two-stage discharge configurations, the internal volume (415) defined by the container/jar walls (413) may be filled with a gas or gas mixture capable of generating excimer molecules and UV-C during the discharge in the jar (e.g., the transition of $Xe_2$ from an excited state to a ground state will emit a UV photon at 172 nm, Ar2 emits at 126 nm, F2 emits at 158 nm, KrCl emits at 222 nm, and XeBr emits at 282 nm). This generation of UV-C can additionally augment plasma sterilization and disinfection of, for example, face masks, bandages etc. For the UV to get through the container or jar, the container or jar walls needs to be made from UVC transparent material (e.g., quartz).

The enhanced formation of radicals due to the chemical reagent layer, displacement current and the charging of the interface between the plasma and hands (or other surface or part of the human body) contribute to sterilization and disinfection of material surfaces by, e.g., the various embodiments described above.

The disclosed devices can be used to disinfect various surfaces, including body parts, clothing, personal items, and protection equipment such as masks. The disclosed devices are preferably hand-held devices suitable for personal use and able to sterilize a variety of surface in several ways. Optionally, the synergistic action of hydrogen peroxide and CAP can be utilized.

In one embodiment, a dielectric barrier discharge (DBD) device as disclosed previously is provided.

A cold homogenous plasma is generated by forming a discharge path the involves, at least, electricity passing from the one or more first electrodes, to the at least one dielectric layer, and then from the dielectric layer to the one or more second electrodes or chemical reagent layers, to ground. As disclosed above, other components may be involved in the discharge path, as appropriate.

The plasma is generally capacitively coupled with the displacement current, generally forming in small gaps (preferably ≤2 mm) that are (i) in or around a grounded electrode or (ii) between the dielectric layer and the grounded electrode (or grounded surface, such as a human hand).

The generated plasma induces reactive species to form on a contaminated surface (containing biological contaminants such as bacteria and/or viruses, etc.) by contacting the contaminated surface with cold homogenous plasma, the contaminated surface containing bacteria, viruses, or a combination thereof. The reactive species are then allowed to kill the reactive species to kill the bacteria, viruses, or combination thereof. In preferred embodiments, the contaminated surface is exposed to the plasma for a period of time of ≤5 minutes, ≤4 minutes, ≤3 minutes, ≤2 minutes, ≤90 seconds, or ≤1 minute.

In some embodiments, a layer of liquid is optionally provided between the DBD device and the contaminated surface, prior to generating the plasma. The liquid is selected/configured to amplify the plasma-induced chemistry. For example, the liquid it could be water, $H_2O_2$, etc., as disclosed previously.

If a shield is provided, the contaminated surfaces preferably come into contact with the shield. For example, if a shield is provided for a hand sterilizer, the shield will be in contact with the user's hand.

Example 2

To demonstrate the disinfection ability of a disclosed device, the effectiveness of the flex-DBD of Example in reducing the bacterial load of *E. coli* 10-beta (New England Biolabs) and the standard *E. coli* AMS 198 (ATCC-11229) was examined. Bacteria were cultured following vendor's instructions at 37° C. in Luria broth or Luria broth agar (both from Research Products International). For the surface test experiments, we used a suspension of the *E. coli* strain (OP-50-GFP, Caenorhabditis Genetics Center) that expresses cytoplas-mic green fluorescent protein and forms a uniform bacterial lawn rather than discrete colonies.

The flex-DBD was attached to a holder, or in other experiments, to the lid of a 60 mm petri dish. The experiments included the treatment of bacteria seeded in petri dishes, on a disposable textile type material, on metal (aluminum), and on glass (microscope cover slips). For treatment of bacterial plates, 50 μl of a fresh bacteria culture was spread on LB-agar plates and the plate surface was treated with the flex-DBD attached to the underside of a lid, placed over the petri dish, for different amounts of time. The plates were incubated overnight at 37° C. and visually compared them to untreated control and examined for areas that were clear of bacteria. To test the disinfection of the textile-type surfaces, 100 μl of *E. coli* OP-50 was spread on textile-like polyethylene material (Tyvek, DuPont). The petri dish cover with the flex-DBD attached was placed over the inoculated area. The petri dish cover used in this experiment was cut to maintain a 1-2 mm distance between the treated surface and the face of the flex-DBD. Each region was treated for a set amount of time and at the end of the treatment time, immediately stamped with an LB contact plate (Carolina Biological Supply Company). The untreated area was stamped as the control. The contact plates were incubated for 24 h at 37° C. Qualitative results were assessed visually by observing GFP expression using a gel imaging station (FastGene Blue/Green LED GelPic Box, Nippon Genetics).

To quantify disinfection, bacteria (*E. coli* 10-beta, Standard *E. coli* AMS 198 or OP50-GFP) were inoculated on glass coverslips (25 mm diameter). Four droplets of 5 μl each (20 μl) of the bacterial culture (starting concentration $10^8$ CFU/ml) were placed onto each coverslip and allowed to dry for approximately 40 min. The slides with dry bacterial culture were then placed onto the flex-DBD with the inoculated side directly in contact with the discharge. The coverslips were treated for 10, 30, 90, and 270 s. At the end of the treatment time, the treated coverslip was placed in a centrifuge tube with 7.5 ml LB, enough to cover the coverslip. The tubes were vortexed on a medium setting for 20 s to recover the bacteria from the treated surface but not damage the cell membrane. The resulting bacterial suspension was spread on LB-agar plates and incubated for 24 h. Cultures were then counted and the number used to calculate the logarithmic reductions of bacterial concentration. All disinfection experiments were conducted with the flex-DBD operating at 3 kV, 20% duty cycle, and 40-50° C.

The efficiency of the flex-DBD disinfection was tested in conjunction with a commonly available 3% solution of $H_2O_2$. The discharge in the flex-DBD is suppressed by water so a semipermeable polyethylene material (Tyvek, DuPont) was used to keep the $H_2O_2$ solution from the surface of the flex-DBD. Pieces of material were disinfected by soaking for 5 min in a 70% solution of isopropyl alcohol then dried thoroughly for at least 30 min. For each trial, a piece of the sterile material was placed on top of the operating flex-DBD and then adding five 2 μl droplets of 3% $H_2O_2$ solution on top of the polyethylene material. An inoculated glass coverslip was placed on top of the solution with the bacteria in contact with the solution. At the end of each treatment, the coverslip and the cloth were dropped into a centrifuge tube with 7.5 ml of LB solution. The same recovery and plating procedure was used in all experiments. The controls for this experiment were inoculated but untreated coverslips, as well as the same procedure with $H_2O_2$ but with the flex-DBD remaining turned off. The disinfection efficiency of $H_2O_2$ aided only by the UV light produced by the flex-DBD was also examined. To block all the output from the plasma except light, a thin film filter transparent down to 190 nm was placed between the DBD and $H_2O_2$. Finally, to eliminate the operation temperature as a factor contributing to the disinfection process, inoculated glass coverslips were placed on a heating block at, e.g., 47° C. and the same disinfection procedures were repeated to determine the reduction in the bacterial load.

To quantify bacterial load reduction, the treated plates were imaged after 24 h of growth and the number of bacterial colonies were counted, interpreted as colony forming units (CFUs) in the plate-seeding solution. When possible, ImageJ (1.53c) software was used to count CFUs, otherwise the counting was done visually. The bacterial load in CFU/ml was calculated by multiplying the CFU count by 9375 (follows from 40 μl spread on each plate from coverslips washing volume of 7.5 ml LB broth, and original inoculation volume of 20 μl), and multiplying to account for any serial dilutions. The logarithmic reduction in the bacterial load was calculated as $\log_{10}(N_0/N)$, where $N_0$ is the bacterial load at CFU/ml without any treatment (0 s coverslip), and N is the bacterial load at CFU/ml at each treatment time. All the experiments were performed in triplicates of samples and plates. Statistical significance between pairs of treatments was evaluated using repeated measures ANOVA.

The pH of the LB broth, Phosphate Buffer Saline solution (Sigma-Aldrich), and the 3% hydrogen peroxide solutions was determined before and after the application of the flex-DBD, using a pH meter (Aspera Instruments, model SX823-B, ±0.01 pH) and pH test strips (Esee, ±0.5) for amounts too small for the pH sensor.

Two indicator strip tests were used to check the $H_2O_2$ production by the plasma, 2-200 ppm range test strips (Industrial Test Systems) to test the production of $H_2O_2$ in ≈20 μl of Luria Broth and a 1-10% range to check the changes in the concentration of in the 3% $H_2O_2$ solution used for the disinfection that combined the flex-DBD and $H_2O_2$.

A scavenger method was used to assess qualitatively the production of the OH in solutions during plasma treatment. Coumarin (>99%, Sigma-Aldrich) was used as a scavenger because it reacts with OH· in solution to produce 7-hydroxy-coumarin that fluoresces at 460 nm when excited at 390 nm. Coumarin itself does not fluoresce in this spectral range. A 5 mM solution of coumarin was prepared in a 20 mM PBS by dissolving crystalline coumarin in the PBS solution at a pH9 and readjusting the pH of the resulting solution back to 7.4 with HCl. Three reference solutions were used: the coumarin stock solution, a solution prepared by adding equal amounts of coumarin solution and PBS, and a solution prepared by adding equal amounts of the coumarin stock solution and 3% hydrogen peroxide. The fluorescence of each solution was recorded at room temperature using an Ocean Optics Fluorescence/Absorption spectrometer. Coumarin/PBS solution and coumarin/hydrogen peroxide solutions were treated with the DBD discharge for 5 min, and the fluorescence of was recorded immediately following the treatment.

To evaluate the effectiveness of the flex-DBD device in decontamination of surfaces from biological contaminants, qualitative and quantitative experiments were performed. The qualitative experiments included the treatment of *E. coli* in petri dishes, the decontamination of inoculated aluminum and fabric surfaces; the quantitative bacterial load reduction was determined by treating bacterial culture dried onto glass coverslips as discussed above. Droplets of the bacterial culture were placed on an aluminum surface, treated by exposure to the flex-DBD, and then stamped with contact plates. The flex-DBD effectively reduced the bacterial load when the DBD was placed 1 mm from the surface and operated at 3 kV and 44 kHz, duty cycle of 20%. The flex-DBD device was also effective at disinfecting textile-type textile-like polyethylene material. To assess the spatial extent of disinfection, the fabric was uniformly inoculated with a transgenic *E. coli* strain that expresses green fluorescent protein (OP-50-GFP) and treated a 10×20 mm area with the same operating parameters remained. Only viable bacteria contain GFP and fluoresce when excited with blue light. Indeed, there was a marked reduction in GFP positive colonies around the treated area. The distance of the DBD from the surface is also important because reducing the distance from 1 mm above the surface to a direct contact with the ground electrode, increased the rate of inactivation of bacteria. A similar spatial pattern was obtained by treating *E. coli* bacterial culture dried onto the surface of a glass coverslip, following 30 s treatment with the flex-DBD.

To quantify the bactericidal effect of the flex-DBD we inoculated and dried glass coverslips and measured the surviving bacterial load in colony forming units per milliliter (CFU/ml) as discussed above. Treatment with the flex-DBD device reduced viable bacteria $\log_{10}(N_0/N)=4.1$ after 90 s. The flex-DBD was operated at a voltage of 3 kV and discharge power of 0.5 $W/cm^2$, and the temperature of the grounded surface was below 50° C. The inactivation of *E. coli* was repeated using the Standard *E. coli* strain AMC 198 (ATCC 11,229). Two experiments were conducted, one using a lower voltage, 2 kV peak voltage and the temperature of the grounded surface T<40° C., and 3 kV peak voltage and T<50° C. The higher applied voltage resulted in faster ($p=0.003$, ANOVA) inactivation of *E. coli*; $\log_{10}(N_0/N)=5.8$ after 180 s treatment as compared to $\log_{10}(N_0/N)=2.6$ after 180 s, demonstrating a dependence on the flex-DBD peak voltage.

The 1 $\log_{10}$ reduction (D value) for *E. coli* AMS 198 was calculated because the data is less variable than that of 10-beta, probably due to a greater control of the strain characteristics. At the start of the plasma treatment, the plasma affects the most susceptible bacteria that is located the closest to the plasma and hence is subjected to shorter-lived reactive plasma species. Hence the inactivation rate is the highest for the short treatment times. A linear fit to the treatment times of 10 s to 270 s give the times for 1 $\log_{10}$ reduction, D=74±2 s with the correlation coefficient, R=0.996.

It was also tested whether the device operating temperature (40° C. and 50° C.) caused disinfection of *E. coli* 10 Beta and *E. coli* AMC 198 strains. Instead of treatment with flex-DBD we incubated contaminated coverslips at 50° C. No reduction in the bacterial load even at the longest exposure times of 180 s and 270 s was found. Therefore, the improvement in the disinfection at higher voltage may be attributed to plasma related effects such as the increase in the concentration of reactive species.

Spectral analysis of the flex-DBD confirms the production of the OH and a wide range of ROS and RNS by the discharge. Hydroxyl radical is the highest oxidizer and it reacts with lipids in the cell membrane and oxidizes proteins and nucleic acids inside the cells. Because of its reactivity, it is very short-lived and needs to be produced at the site of action. Since the inoculated coverslips were in contact with the patterned side of the flex-DBD during treatment, we can speculate that the reactions of OH· and other short-lived ROS are responsible for the fast initial rate of bacterial inactivation. Ozone and nitrogen oxides evident in the IR absorption spectrum can diffuse into the substrate and continue the disinfection process at a slower rate limited by the rate of diffusion and cellular processes.

To augment the disinfection, the flex-DBD treatment was applied in combination with 3% $H_2O_2$ solution commonly available and, widely used for oral, skin, and wound disinfection. Applying the DBD together with $H_2O_2$ results in a 3.5 $\log_{10}$ reduction in the bacterial population in just 10 s and in >5 $\log_{10}$ reduction in 90 s. The combined disinfection effect of hydrogen peroxide and plasma is faster than either DBD alone ($p=0.04$, repeated measures ANOVA test) or $H_2O_2$ alone ($p=0.03$).

The antibacterial mechanism of $H_2O_2$ solutions alone is based on the production of the highly reactive hydroxyl radicals, but there is no appreciable equilibrium concentration of OH· in the solution itself. A chemical scavenger method was used to detect the presence of the OH· radical in 3% $H_2O_2$ solution and found that the concentration is of the same order as coumarin/PBS solutions that contain no hydrogen peroxide. The hydroxyl radical can be produced inside a cell by the Fenton reaction:

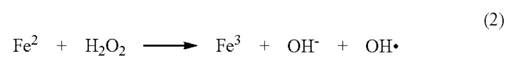

(2)

The production of OH leads to oxidation and eventually to cell death. This disinfection by $H_2O_2$ alone depends on the concentration of the solution and can be concentration limited, slowing down as the hydrogen peroxide is used up.

The results of these tests show that a bacterial load reduction due to the $H_2O_2$ alone slows down faster than the corresponding DBD treatment (the times for 1 $\log_{10}$ reduction, D=139±5 s, R=0.97 for *E. coli* 10-beta; and D=135±5 s, R=0.947 for *E. coli* AMC 198). The sustained rate of reduction increases to D=40 s (R=0.86) when the treatment is carried out by both the DBD and the $H_2O_2$ solution and reaches a >6 $\log_{10}$ reduction in just 90 s. In humid environments, air plasma produces hydroxyl radicals generally through the interactions of electrons and excited nitrogen with water vapor. But the hydroxyl radical reacts, oxidizes or recombines to form hydrogen peroxide on a microsecond scale, which then diffuses into the solution, thus resulting in the production of $H_2O_2$ in the solution. The results of the indicator experiments support the increase of $H_2O_2$ concentration in both the Luria broth used for the *E. coli* suspensions and in the $H_2O_2$ solution used in the experiments with flex-DBD and $H_2O_2$. The application of flex-DBD to Luria broth for 90 s increases the concentration of $H_2O_2$ (and other oxidizing agents) to at least 100 ppm. Applying the flex-DBD directly to the $H_2O_2$ solution for 90 s treatment time, the concentration of increases the concentration of $H_2O_2$ from 3% before treatment to 5-10% after treatment.

Plasma can generate $H_2O_2$ in water solutions but the UV radiation from the plasma can also decompose the existing $H_2O_2$. To test whether the UV radiation from the flex-DBD was sufficient to explain the improved *E. coli* inactivation with $H_2O_2$, all plasma products were blocked except for the UV radiation with a UV filter. UV radiation improved the inactivation of bacteria in the first 30 s compared with $H_2O_2$ alone, but it did not achieve any additional reduction with increasing treatment time. After the first 30 s, the survival curve flattens (D>250 s). This effect of UV radiation is insufficient to explain the improvement in the inactivation with $H_2O_2$ achieved by the addition of the DBD plasma. Hence the plasma, not UV radiation alone, improves the action of $H_2O_2$.

The remarkable synergy between plasma and $H_2O_2$ can be explained by the combination of the peroxone process with the RNS produced by the flex-DBD. The IR absorption spectrum is dominated by ozone and RNS. Peroxone is an advanced oxidation process that has been known for over 100 years. It involves the reactions of ozone and hydrogen peroxide that promote the production of OH·, which is a much more effective oxidizer than ozone alone. Plasma-generated superoxide can also aid in the process of generating OH· in solution. The scavenger method shows that plasma generates not only a stable hydrogen peroxide in a liquid solution but a measurable OH· concentration. Plasma treatment of a $H_2O_2$ solution results in a significant increase in the concentration of OH· in solution, well above plasma treatment alone. OH· oxidation can lead to an easier penetration of the membrane by RNS that damage the proteins inside the cell and improve the overall disinfection process. Hence the combination of plasma treatment with hydrogen peroxide is a powerful tool for disinfection of bacterial contaminants.

Further, a flexible DBD device was tested for antiviral capability. There were two sets of experiments, those that used the dry suspension, and those that used a liquid virus suspension without drying. In the first experiments, droplets of a virus suspension were placed in a polyurethane petri dish, 8-2 uL droplets in each dish, and let dry for 15-20 min, until visually dry. The dishes were placed upside down on top of the DBD with the dry virus suspension facing the discharge. The treatment times were 30 s, 1 min, 2 min, and 4 min. In addition to the dry suspension, the effectiveness of the flex-DBD was tested against viruses in a liquid suspension. The same amount of virus suspension was placed in each petri dish as in previous experiments. The flex-DBD was placed 1 mm above the surface of the droplets of the liquid suspension with the help of a mechanical positioner and held in place for the treatment times of 1 min, 2 min, and 4 min. The droplets of the liquid suspension were kept in a petri dish for the same time as a treated sample but without plasma exposure, hence there was a separate control sample for each time point.

The log reduction in viable virus concentration was relatively linear over the four minutes period. The viable virus concentration was calculated as $\text{Log}_{10} N_0/N_t$, where $N_0$ is the number of plaque forming units (PFU) per $cm^3$ in the control (untreated) liquid or dry suspension and $N_t$ is the PFU/$cm^3$ in the samples treated for a time t. The exposure to the DBD for 4 min at the same operating conditions as for the antibacterial experiments with *E. coli*, resulted in the reduction of viable virus concentration of 93% ($\text{Log}_{10} N_0/N_t$=1.7) for the dry suspension and 99.7% ($\text{Log}_{10} N_0/N_t$=2.3) for the liquid suspension.

Those skilled in the art will recognize or be able to ascertain using no more than routine experimentation many equivalents to the specific embodiments of the invention described herein. Such equivalents are intended to be encompassed by the following claims.

What is claimed is:

1. A dielectric barrier discharge (DBD) device, comprising:

one or more first electrodes;

one or more second electrodes or chemical reagent layers;

at least one flexible dielectric layer between the one or more first electrodes and the one or more second electrodes or chemical reagent layers;

a first semipermeable layer in contact with an outward-facing surface of the first electrode;

a second semipermeable layer in contact with the outward-facing surface of the one or more second electrodes, wherein the at least one dielectric layer is in contact with a planar surface of the one or more first electrodes on a first surface of the at least one flexible dielectric layer, and is in contact with a planar surface of the one or more second electrodes or chemical reagent layers on an opposite surface of the at least one flexible dielectric layer, wherein the DBD device is configured to function without fluid flow, wherein the one or more first electrodes and the at least one dielectric layer are flexible, and wherein the DBD device is configured to ignite surface dielectric barrier discharges.

2. The dielectric barrier discharge (DBD) device according to claim 1, wherein the one or more second electrodes or chemical reagent layers are one or more second electrodes, and each one or more second electrode is configured as a wire or a patterned metal layer.

3. The dielectric barrier discharge (DBD) device according to claim 1, wherein the first and second semipermeable layers are a dielectric fabric or mesh.

4. The dielectric barrier discharge (DBD) device according to claim 1, wherein the DBD device is powered by a portable power supply.

5. The dielectric barrier discharge (DBD) device according to claim 1, wherein a current used by the DBD device is less than or equal to 2 mA.

6. The dielectric barrier discharge (DBD) device according to claim 1, wherein the temperature of the device is between about 22° C. and about 40° C.

7. The dielectric barrier discharge (DBD) device according to claim 1, wherein the one or more second electrodes are a patterned metal layer.

8. The dielectric barrier discharge (DBD) device according to claim 1, wherein the one or more second electrodes or chemical reagent layers is a chemical reagent layer.

9. The dielectric barrier discharge (DBD) device according to claim 1, wherein an internal volume defined by dielectric layer is filled with a gas or gas mixture capable of generating excimer molecules and UV-C during a discharge by the device.

10. The dielectric barrier discharge (DBD) device according to claim 1, wherein the one or more second electrodes are a patterned metal layer in contact with the dielectric layer, and wherein the DBD device is configured to ignite surface dielectric barrier discharges between two parts of the patterned metal layer.

11. The dielectric barrier discharge (DBD) device according to claim 1, wherein the DBD device is free of gaps between adjacent layers.

* * * * *